United States Patent
Chiou et al.

(10) Patent No.: US 7,803,543 B2
(45) Date of Patent: Sep. 28, 2010

(54) METHODS AND KITS FOR THE DETECTION OF NUCLEOTIDE MUTATIONS USING PEPTIDE NUCLEIC ACID AS BOTH PCR CLAMP AND SENSOR PROBE

(75) Inventors: Chiuan-Chian Chiou, Changhua Hsien (TW); Ji-Dung Luo, Miao-Li Hsien (TW)

(73) Assignee: Chang Gung University, Tao-Yuan (TW)

( * ) Notice: Subject to any disclaimer, the term of this patent is extended or adjusted under 35 U.S.C. 154(b) by 395 days.

(21) Appl. No.: 11/624,796

(22) Filed: Jan. 19, 2007

(65) Prior Publication Data

US 2008/0176226 A1 Jul. 24, 2008

(51) Int. Cl.
*C12Q 1/68* (2006.01)
(52) U.S. Cl. .......................... 435/6; 435/91.2
(58) Field of Classification Search .................. None
See application file for complete search history.

(56) References Cited

U.S. PATENT DOCUMENTS

| 5,539,082 | A | 7/1996 | Nielsen et al. |
| 7,081,336 | B2 | 7/2006 | Bao et al. |
| 2004/0014105 | A1 | 1/2004 | Schroeder et al. |
| 2004/0091905 | A1 | 5/2004 | Guo |

FOREIGN PATENT DOCUMENTS

| WO | WO 92/20702 | 11/1992 |
| WO | WO 92/20703 | 11/1992 |

OTHER PUBLICATIONS

Dabritz et al. (British Journal of Cancer, 2005, vol. 92, p. 405-412, IDS reference).*
Luo et al. (Nucleic Acids Research, 2006, vol. 34, No. 2, e12, p. 1-7).*
Chen et al. (Clin. Chem, 2004, vol. 50, p. 481-489).*
Molenaar et al. (EMBO Journal, 2003, 22(24):6631-6641).*
Kostrikis, et al., "Spectral Genotyping of Human Alleles", Science, vol. 279, p. 1228-1229, Feb. 20, 1998.
Wang, et al., "Unique K-*ras* Mutational Pattern in Pancreatic Adenocarcinoma from Taiwanese Patients", Cancer Letter, vol. 180, p. 153-158, 2002.
Braasch, et al., "Locked Nucleic Acid (LNA): Fine-tuning the recognition of DNA and RNA", Chemistry & Biology, vol. 8, p. 1-7, 2001.

(Continued)

*Primary Examiner*—Gary Benzion
*Assistant Examiner*—Stephanie K Mummert
(74) *Attorney, Agent, or Firm*—Hunton & Williams LLP

(57) ABSTRACT

Disclosed herein is a method for determining whether a target polynucleotide sequence contained in a nucleic acid sample has nucleotide variation(s) in a selected region thereof, the steps of which involve the use of a pair of primers that allows the formation of a PCR product having a sequence covering that of the selected region of the target polynucleotide sequence via a PCR process, and a peptide nucleic acid (PNA) that acts as a PCR clamp as well as a sensor probe. Also disclosed herein is a kit for use in determining the presence of nucleotide variation(s) in the target polynucleotide sequence, which includes the pair of primers and the PNA.

23 Claims, 4 Drawing Sheets

OTHER PUBLICATIONS

Bird, "The Essentials of DNA Methylation", Cell, vol. 70, p. 5-8, Jul. 10, 1992.

Chiou, et al., "Single-Tube Reaction using Peptide Nucleic Acid as both PCR Clamp and Sensor Probe for the detection of rare mutations", Nature Protocols, vol. 1, No. 6, p. 2604-2612, 2006.

Luo, et al., "Detection of Rare Mutant K-ras DNA in a single-tube reaction using peptide nucleic acid as both PCR clamp and sensor probe", Nucleic Acids Research, vol. 34, No. 2, p. 1-7, 2006.

Srivastava, et al., "Biomarkers for Early Detection of Colon Cancer", Clinical Cancer Research, vol. 7, p. 1118-1126, May 2001.

Hirsch, et al., "Early Detections of Lung Cancer: Clinical Perspectives of Recent Advances in Biology and Radiology", Clinical Cancer Research, vol. 7, p. 5-22, Jan. 2001.

Chen, et al., "Rapid Detection of K-ras Mutations in Bile by Peptide Nucleic Acid-mediated PCR Clamping and Melting Curve Analysis: Comparison with Restriction Fragment Length Polymorphism Analysis", Clinical Chemistry, vol. 50, No. 3, p. 481-489, 2004.

Motojima, et al., "Mutations in the Kirsten-ras Oncogene are common but Lack Correlation with Prognosis and Tumor Stage in Human Pancreatic Carcinoma", The American Journal of Gastroenterology, vol. 86, No. 12, p. 1784-1788, 1991.

Dieterle, et al., "Detection of Isolated Tumor Cells by Polymerase Chain Reaction-Restriction Fragment Length Polymorphism for K-ras Mutations in Tissue Samples of 199 Colorectal Cancer Patients", vol. 10, p. 641-650, Jan. 15, 2004.

Anker, et al., "K-ras Mutations are found in DNA Extracted from the Plasma of Patients with Colorectal Cancer", Gastroenterology, vol. 112, p. 1114-1120, 1997.

Iinuma, et al., "Detection of Tumor Cells in Blood using CD45 Magnetic Cell Separation followed by Nested Mutant Allele-Specific Amplification of p53 and K-ras Genes in Patients with Colorectal Cancer", Int. J. Cancer (Pred. Oncol.), vol. 89, p. 337-344, 2000.

Jacobson, et al., "A Highly Sensitive assay for Mutant ras genes and its application to the study of presentation and relapse genotypes in acute leukemia", Oncogene, vol. 9, p. 553-563, 1994.

Andersen, et al., "K-ras Mutations and HLA-DR expression in Large bowel adenomas", British Journal of Cancer, vol. 74, p. 99-108, 1996.

Nickerson, et al., Automated DNA diagnostics using an ELISA-based oligonucleotide ligation assay, Proc. Natl. Acad. Sci. USA, vol. 87, p. 8923-8927, Nov. 1990.

Nishikawa, et al., "A simple method of detecting K-ras point Mutations in stool samples for colorectal cancer screening using one-step polymerase chain reaction/restriction fragment length polymorphism analysis", Clinica Chimica Acta, vol. 318, p. 107-112, 2002.

Toyooka, et al., "Detection of Codon 61 Point Mutations of the Kras Gene in Lung and Colorectal Cancers by enriched PCR", Oncology Reports, vol. 10, p. 1455-1459, 2003.

Imai, et al., "K-ras Codon 12 Mutations in Biliary Tract Tumors Detected by Polymerase Chain Reaction Denaturing Gradient Gel Electrophoresis", Cancer, vol. 73, No. 11, p. 2727-2733, Jun. 1, 1994.

Lilleberg, et al., "High Sensitiivity Scanning of Colorectal Tumors and Matched Plasma DNA for Mutations in APC, TP53, K-RAS, and BRAF Genes with a Novel DHPLC Fluorescence Detection Platform", Ann. N.Y. Acad. Sci., vol. 1022, p. 250-256, 2004.

Lleonart, et al., "Sensitive and Specific detection of K-ras Mutations in colon tumors by short oligonucleotide mass analysis", Nucleic Acids Research, vol. 32, No. 5, p. 1-8, 2004.

Sun, et al., "Detection of Tumor Mutations in the Presence of Excess amounts of Normal DNA", Nature Biotechnology, vol. 19, p. 186-189, Feb. 2002.

Nakao, et al., "Rapid and reliable detection of N-ras mutations in acute lymphoblastic leukemia by melting curve analysis using LightCycler technology", Leukemia, vol. 14, p. 312-315, 2000.

Pincas, et al., "High Sensitivity EndoV mutation scanning through real-time ligase proofreading", Nucleic Acids Research, vol. 32, No. 19, p. 1-13. 2004.

Maekawa, et al., "Three-Dimensional Microarray Compared with PCR-Single-Strand Conformation Polymorphism Analysis/DNA Sequencing for Mutation Analysis of K-ras Codons 12 and 13", Clinical Chemistry, vol. 50, No. 8, p. 1322-1327, 2004.

Demers, et al., "Enhanced PCR Amplification of VNTR Locus D1S80 using Peptide nucleic acid (PNA)", Nucleic Acids Research, vol. 23, No. 15, 3050-3055, 1995.

Nielsen, et al., "Sequence-Selective Recognition of DNA by Strand Displacement with a Thymine-Substituted Polyamide", Science, vol. 254, p. 1497-1500, Dec. 6, 1991.

Hanvey, et al., "Antisense and Antigene Properties of Peptide Nucleic Acids", Science, vol. 258, p. 1481-1485, Nov. 27, 1992.

Egholm, et al., "PNA hybridizes to complementary oligonucleotides obeying the Watson-Crick hydrogen-bonding rules", Nature, vol. 365, p. 566-568, Oct. 7, 1993.

Kyger, et al., "Detection of the Herditary Hemochromatosis Gene Mutation by Real-Time Fluorescene Polymerase Chain Reaction and Peptide Nucleic Acid Clamping", Analytical Biochemistry, vol. 260, p. 142-148, 1998.

Thiede, et al., "Simple and Sensitive detection of Mutations in the ras Proto-oncogenes using PNA-mediated PCR clamping", Nucleic Acids Research, vol. 24, No. 5, p. 983-984, 1996.

Taback, et al., "Peptide Nucleic Acid Clamp PCR: a Novel K-ras Mutation Detection Assay for Colorectal Cancer Micrometastases in Lymph Nodes", Int. J. Cancer, vol. 111, p. 409-414, 2004.

Ørum, et al., "Single base pair mutation analysis by PNA directed PCR clamping", Nucleic Acids Research, vol. 21, No. 23, p. 5332-5336, 1993.

Karadag, et al., "A Noel technique based on a PNA hybridization probe and FRET principle for quantification of mutant genotype in fibrous dysplasia/McCune-Albright Syndrome", Nucleic Acids Research, vol. 32, No. 7, p. 1-10, 2004.

Hancock, et al., "Design and Use of a Peptide Nucleic Acid for Detection of the Heteroplasmic Low-Frequency Mitochondrial Encephalomyopathy, Lactic Acidosis, and Stroke-like Episodes (MELAS) Mutation in Human Mitochondrial DNA", Clinical Chemistry, vol. 48, No. 12, p. 2155-2163, 2002.

Takiya, et al., "Identification of Single Base-pair Mutation on uidA Gene of Escherichia coli O157:H7 by Peptide Nucleic Acids (PNA) Mediated PCR Clamping", Biosci. Biotechnol. Biochem., vol. 68, No. 2, p. 360-368, 2004.

Kirishima, et al., "Detection of YMDD Mutant Using a novel Sensitive Method in Chronic liver disease type B patients before and during lamivudine treatment", Journal of Hepatology, vol. 37, p. 259-265, 2002.

Ohishi, et al., "Identification of Rare Polymerase Variants of Hepatitis B Virus Using a Two-Stage PCR with Peptide Nucleic Acid clamping", Journal of Medical Virology, vol. 72, p. 558-565, 2004.

Bernard, et al., "Homogeneous Multiplex Genotyping of Hemochromatosis Mutations with Fluorescent Hybridization Probes", American Journal of Pathology, vol. 153, No. 4, p. 1055-1061, Oct. 1998.

Däbritz, et al., "Detection of Ki-ras mutations in tissue and plasma samples of patients with pancreatic cancer using PNA-mediated PCR clamping and hybridisation", British Journal of Cancer, vol. 92, p. 405-412, 2005.

Kreuzer, et al., "Preexistence and evolution of imatinib mesylate-resistant clones in chronic myelogenous leukemia detected by a PNA-based PCR clamping technique", Ann. Hematol., vol. 82, p. 284-289, 2003.

Chiou, et al., "Detection of Trace Amounts of Mutant K-ras DNA by Peptide Nucleic Acid as Both PCR Clamp and Sensor Probe", Poster Session Abstracts of the San Diego Conference Cool Tools and Hot Applications, Nov. 18-20, 2004, San Francisco, CA.

Lay, et al., "Real-time Fluorescence genotyping of factor V Leiden during rapid-cycle PCR", Clinical Chemistry, vol. 43, No. 12, p. 2262-2267, 1997.

Rodriguez-Manotas, et al., "Real Time PCR Assay with Fluorescnet hybridization probes for genotyping intronic polymorphism in presenilin-1 gene", Clinica Chimica Acta, vol. 364, p. 343-344, 2006.

Popp, et al., "High-Speed genotyping of CYP1A2*1F Mutation with Fluorescent Hybridization probes using the LightCycler", Pharmacogenomics, vol. 4, No. 5, p. 643-646, 2003.

Nagai, et al., "Genetic Heterogeneity of the Epidermal Growth Factor Receptor in Non-Small Cell Lung Cancer Cell Lines Revealed by a Rapid and Sensitive Detection System, the Peptide Nucleic Acid-Locked Nucleic Acid PCR Clamp", Cancer Res., vol. 65, No. 16, p. 7276-7282, Aug. 15, 2005.

Holliday, et al., "DNA methylation and mutation", Mutation Research, vol. 285, p. 61-67, 1993.

Bird, "CpG-rich islands and the function of DNA methylation", Nature, vol. 321, p. 209-213, May 15, 1986.

Jones, et al., "Cancer epigenetics comes of age", Nature Genetics, vol. 21, p. 163-167, Feb. 1999.

Baylin, et al., "Alterations in DNA Methylation: A Fundamental Aspect of Neoplasia", Advances in Cancer Research, vol. 72, p. 141-196, 1998.

Feinberg, "DNA Methylation, Genomic Imprinting and Cancer", Curr. Top. Microbiol. Immunol., vol. 249, p. 87-99, 2000.

Wang, et al., "Comparison of bisulfite modification of 5-methyldeoxycytidine and deoxycytidine residues", Nucleic Acids Research, vol. B, No. 20, p. 4777-4790, 1980.

Hyrup, et al., "Peptide Nucleic Acids (PNA): Synthesis, Properties and Potential Applications", Bioorganic & Medicinal Chemistry, vol. 4, No. 1, p. 5-23, 1996.

Heesen, et al., "Rapid and reliable genotyping for the Toll-like receptor 4 A896G polymorphism using fluorescence-labeled hybridization probes in a real-time polymerase chain reaction assay", Clinica Chimica Acta, vol. 333, p. 47-49, 2003.

* cited by examiner ns and Kits for the Detection of Nucleotide Mutations Using Peptide Nucleic Acid as Both PCR Clamp and Sensor Probe

BACKGROUND OF THE INVENTION

1. Field of the Invention

This invention primarily relates to a method for determining whether a target polynucleotide sequence contained in a nucleic acid sample has nucleotide variation(s) in a selected region thereof, the steps of which involve the use of a pair of primers that allows the formation of a PCR product having a sequence covering that of the selected region of the target polynucleotide sequence via a PCR process, and a peptide nucleic acid (PNA) that acts as a PCR clamp as well as a sensor probe. This invention also relates to a kit for use in determining the presence of nucleotide variation(s) in the target polynucleotide sequence, which comprises the pair of primers and the PNA.

2. Description of the Related Art

Somatic mutations are present in various proportions in numerous developmental pathologies. Many diseases such as hemophilia, Albright syndrome (MAS), Alzheimer's disease, Huntington's disease, Duchenne muscular dystrophy (DMD), cystic fibrosis, etc., and a number of tumor pathologies are characterized by nucleotide variation(s) in the sequences of particular genes. These mutations/nucleotide variations may lead to a specific pathology when numbers of cells expressing the same reach a critical level.

Somatic mutations have been reported to be useful markers for early detection of cancers (S. Srivastava et al. (2001), *Clin. Cancer Res.*, 7:1118-1126; F. R. Hirsch et al. (2001), *Clin. Cancer Res.*, 7:5-22). For example, the K-ras gene, which encodes a 21-kDa GTP-binding protein, controls the mechanisms of cell growth and differentiation (C. Y. Chen et al. (2004), *Clin. Chem.*, 50:481-489). The K-ras mutation in codons 12 and 13 occurs in 80-90% of pancreatic cancer and 35-50% of colorectal cancer (K. Motojima et al (1991), *Am. J. Gastroenterol.*, 86:1784-1788; C. P. Dieterle et al. (2004), *Clin. Cancer Res.*, 10:641-650; P. Anker et al. (1997), *Gastroenterology*, 112:1114-1120).

The major problem of using somatic mutations as markers of malignancy is that the clinical samples, especially body fluids or stools, frequently contain a trace amount of mutant DNA(s) in a large excess of wild-type DNA. The excess of wild-type DNA can exhaust essential reagents during PCR, and tends to mask the mutant DNA's signal during detection assays. The general strategy used to date to overcome this problem is to employ suppression of the wild-type allele or enrichment of the mutant allele during PCR amplification, followed by using a detection procedure that provides a sufficient resolution to reveal the mutant DNA's signal.

Methods used to enrich mutant template level include allele-specific amplification (H. linuma et al. (2000), *Int. J. Cancer*, 89:337-344), restriction enzyme digestion of wild-type DNA (C. P. Dieterle et al., (2004), supra; D. R. Jacobson and N. E. Mills (1994), *Oncogene*, 9:553-563; S. Norheim Andersen et al. (1996), *Br. J. Cancer*, 74:99-108), and sequence-specific ligation (D. A. Nickerson et al. (1990), *Proc. Natl. Acad. Sci. USA*, 87:8923-8927). These methods usually require subsequent procedures to detect mutant DNA's signal, including: (i) distinguishing the conformational or length differences by gel electrophoresis (T. Nishikawa et al. (2002), *Clin. Chim. Acta*, 318:107-112; S. Toyooka et al. (2003), *Oncol. Rep.*, 10:1455-1459; M. Imai et al. (1994), *Cancer*, 73:2727-2733) or denaturing high-performance liquid chromatography (S. L. Lilleberg et al. (2004), *Ann. N Y Acad. Sci.*, 1022:250-256); (ii) detecting short sequences by mass spectrometry (M. E. Lleonart et al. (2004), *Nucleic Acids Res.*, 32, e53; X. Sun et al. (2002). *Nat. Biotechnol.*, 20-186-189); and (iii) detecting nucleotide sequence changes by melting curve analysis (M. Nakao et al. (2000), *Leukemia*, 14:312-315), endonuclease V reaction (H. Pincas et al. (2004), *Nucleic Acids Res.*, 32, e148) or hybridization on a microarray chip (M. Maekawa et al. (2004), *Clin. Chem.*, 50:1322-1327). However, most of these methods are inconvenient for use in clinical laboratories due to multiple manipulations that are time-consuming and cost-inefficient. Most importantly, these methods increase the risk of contamination during multiple transfers.

Recently, the peptide nucleic acid (PNA)-based PCR procedure has been developed for the enrichment of mutant alleles (D. B. Demers et al., (1995), *Nucleic Acids Res.*, 23:3060-3055). PNA is a synthetic DNA analog in which the normal phosphodiester backbone is replaced with a N-(2-aminoethyl)glycine chain. Its nucleobases complement DNA or RNA in the normal A-T and G-C geometry (P. E. Nielsen et al. (1991), *Science*, 254: 1497-1500; J. C. Hanvey et al. (1992), *Science*, 258:1481-1485; M. Egholm et al. (1993), *Nature*, 365:566-568). With the artificial backbone, PNA is resistant to nuclease activities.

Two important features make PNA a superior PCR clamp for specific alleles. It cannot serve as a primer for polymerization, nor can it be a substrate for exonuclease activities of Taq polymerase. In addition, the melting temperature ($T_m$) of a perfectly matched PNA-DNA duplex is higher than that of a DNA-DNA duplex with the same length PNA-DNA duplex is more stable than DNA-DNA duplex. A single mismatch in the PNA-DNA hybrid will cause a $T_m$ drop of 10-18° C., which is much higher than that of the DNA-DNA duplex (E. M. Kyger et al. (1998), *Anal. Biochem.*, 260:142-148). Therefore, within an appropriate temperature range, PNA can specifically block primer annealing or chain elongation on a perfectly matched template without interfering with reactions on templates with mismatched base(s) (X. Sun et al. (2002), supra; C. Thiede et al. (1996), *Nucleic Acids Res.*, 24:983-984; Taback, B. et al. (2004), *Int. J. Cancer*, 111:409-414), which is known as "PNA-mediated PCR clamping" (H. Orum et al., (1993), *Nucleic Acids Res.*, 21:5332-5336). In addition, the large $T_m$ difference between perfectly matched and mismatched hybrids makes PNA a good sensor of point mutations. For example, a PNA sensor probe has been used to detect GNAS mutations after PCR (A. Karadag et al. (2004), *Nucleic Acids Res.*, 32, e63).

PNA-mediated PCR clamping has been widely used for enrichment of rare mutant polynucleotides, including mutations in K-ras gene (B. Taback et al. (2004), supra.) and in mitochondrial DNA (D. K. Hancock et al. (2002), *Clin. Chem.*, 48-2155-2163), the uidA gene of *Escherichia coli* O157:H7 strain (T. Takiya et al. (2004), *Biosci. Biotechnol. Biochem.*, 68:360-368), and the DNA polymerase gene of hepatitis B virus (T. Kirishima et al. (2002), *J. Hepatol.*, 37:259-265; W. Ohishi et al. (2004), *J. Med. Virol.*, 72:558-565).

US Patent Application Publication No. 2004/0014105A1 discloses methods for the selective enrichment of low-abundance polynucleotides in a sample. The method uses enzymatically non-extendable nucleobase oligomer (e.g., PNA) as a PCR clamp to selectively block polymerase activity on high abundance species in the sample, thereby resulting in an enrichment of less abundant species in the sample.

US Patent Application Publication No. 2004/0091905A1 discloses a method for detecting a mutant polynucleotide in a mixture of mutant polynucleotides, wild-type polynucleotides and unrelated polynucleotides. The method uses an extension primer complementary to a first target sequence in both the wild-type and mutant polynucleotides. The method further uses a blocking probe (e.g., PNA probe) complementary to a second target sequence in the wild-type polynucleotides but not in the mutant polynucleotides. Extension of the primers annealed to the first target sequence in mutant polynucleotides produces long extension products. Extension of the primers annealed to the first target sequence in wild-type polynucleotides is blocked by the blocking probe annealed to the second target sequence. Short extension products or no extension products are produced. The extension products are isolated and used in a polymerase chain reaction (PCR). The PCR preferentially amplifies the long extension products.

The use of melting curve analysis in combination with hybridization probe system provides a powerful tool for the detection of single base alterations. The hybridization probe system is most widely used for this purpose. This system usually comprises a pair of oligonucleotides, i.e., the anchor and the sensor, each labeled with a different fluorescent dye, such that fluorescence energy transfer occurs between the two when they anneal adjacent sites of a complementary PCR strand (P. S. Bernard et al. (1998), *Am. J. Pathol.,* 153:1055-1061). The melting curve profile of the sensor probe that is designed to anneal to the variable region of a target gene allows for homogeneous genotyping in a closed tube (P. S. Bernard et al. (1998), supra).

Recently, C. Y. Chen et al. developed a one-step PCR technique using fluorescent hybridization probes and competing peptide nucleic acid oligomers to detect K-ras mutations in bile and to compare the efficacy with restriction fragment length polymorphism (RFLP) analysis (C. Y. Chen et al. (2004), *Clin. Chem.,* 50:481-489). J. Däbritz et al. combined the PCR-clamping approach with melting curve analysis using mutant specific hybridization probes and wild-type specific peptide nucleic acids (PNAs) to determine the genotypes of the most frequent point mutation in codon 12 of the proto-oncogene Ki-ras in tissue and plasma samples of patients with pancreatic cancer (J. Däbritz et al. (2005), *Br. J. Cancer,* 92:405-412). In addition, hybridization probes have been combined with PNA-mediated PCR clamping for detection of variant bcr-abl allele in leukemia (K. A. Kreuzer et al. (2003), *Ann. Hematol.,* 82:284-289). Their studies demonstrated that use of a PNA clamp in combination with a pair of hybridization probes in PCR allows for a homogeneous detection of rare mutant DNA in a closed tube. However, in their designs, the added PNA competed for DNA binding with the sensor probe. The sensor probe therefore should be mutation-specific, i.e., it complements one of the mutant alleles instead of the wild-type allele. This leads to a disadvantage that the mutation-specific probe limits the types of mutations that may be detected. As a consequence, for a selected target gene, a variety of probes need to be synthesized if more than one type of mutations are expected to occur in the selected target gene. These probes have to be tested for their efficiency and compatibility when used together in the same reaction.

In a previous study, the applicants developed a simple method to detect trace amounts of K-ras mutants by using PNA as both PCR clamp and hybridization probe in a capillary PCR reaction, in which a 17-mer PNA complementary to wild type sequence and spanning the codons 12 and 13 of K-ras oncogene was used to clamp PCR for the wild type allele but not mutant alleles. Moreover, the PNA was labeled with a fluorescent dye and used as a sensor probe. The mutant PCR products, with a mismatch to the PNA probe, have a $T_m$ about 10° C. lower than that of the wild-type product (Ch-iuan-Chian Chiou and Ji-Dung Luo, Detection of Trace Amounts of Mutant K-ras DNA by Peptide Nucleic Acid as Both PCR Clamp and Sensor Probe, Poster Session Abstracts of The San Diego Conference Cool Tools and Hot Applications Nov. 18-20, 2004 San Francisco, Calif.).

While this method allows the amplification of trace mutant polynucleotide(s) in the existence of 1,000-fold wild-type polynucleotides, its sensitivity and reproducibility is poor. Therefore, the applicants endeavored to develop an improved method for detecting mutant polynucleotide(s) in clinical samples.

In the present invention, the applicants surprisingly found that the extension temperature and the position of PCR primers have great influences on the efficiency of PNA-mediated PCR clamping. Based on these new findings, it is possible to develop a method with high sensitivity for detecting trace mutant polynucleotide(s). The newly devised method also proves to have excellent reproducibility and, hence, can serve as a useful tool for detecting nucleotide variation(s) in a variety of organisms and for screening rare mutation(s) in many diseases such as cancers.

SUMMARY OF THE INVENTION

Therefore, according to a first aspect, this invention provides a method for determining whether a target polynucleotide sequence contained in a nucleic acid sample has nucleotide variation(s) in a selected region thereof, comprising the steps of:

providing a pair of a first primer and a second primer which allows the formation of a PCR product having a sequence covering that of the selected region of the target polynucleotide sequence via a PCR process, the first primer having a sequence identical to that of a first region located upstream of the selected region of the target polynucleotide sequence, the second primer having a sequence based on that of a second region located downstream of the selected region of the target polynucleotide sequence, wherein the 6'-end of the sequence of the first region is spaced apart from the 5'-end of the sequence of the sequence of the selected region by 30 nucleotides or more;

providing a detectable peptide nucleic acid probe having a sequence that complements fully the sequence of the selected region of the target polynucleotide sequence having no nucleotide variation(s) therein, such that hybridization of the detectable peptide nucleic acid probe to the selected region of the target polynucleotide sequence having no nucleotide variation(s) results in the formation of a duplex having a melting temperature;

determining the melting temperature of the duplex;

admixing the detectable peptide nucleic acid probe and the pair of the first primer and the second primer with the nucleic acid sample to form a mixture;

subjecting the mixture to a PCR process including an extension reaction set to run at a temperature lower than the melting temperature of the duplex by 5 to 20° C., such that a mixture of PCR products is obtained; and subjecting the mixture of PCR products thus-obtained to a melting analysis to determine melting temperatures of the PCR products, wherein the presence of at least one melting temperature lower than the melting temperature of the duplex is indicative of the nucleotide variation(s) in the selected region of the target polynucleotide sequence contained in the nucleic acid sample.

In a second aspect, this invention provides a kit for determining whether a target polynucleotide sequence contained in a nucleic acid sample has nucleotide variation(s) in a selected region thereof, comprising:

a detectable peptide nucleic acid probe having a sequence that complements fully the sequence of the selected region of the target polynucleotide sequence having no nucleotide variation(s) therein, such that hybridization of the detectable peptide nucleic acid probe to the selected region of the target polynucleotide sequence having no nucleotide variation(s) results in the formation of a duplex having a melting temperature;

a pair of a first primer and a second primer which allows the formation of a PCR product having a sequence covering that of the selected region of the target polynucleotide sequence via a PCR process, the first primer having a sequence identical to that of a first region located upstream of the selected region of the target polynucleotide sequence, the second primer having a sequence based on that of a second region located downstream of the selected region of the target polynucleotide sequence, wherein the 5'-end of the sequence of the first region is spaced apart from the 5'-end of the sequence of the sequence of the selected region by 30 nucleotides or more; and an instruction sheet providing guidance for a user to use the detectable peptide nucleic acid probe and the pair of the first primer and the second primer in a method as described above.

BRIEF DESCRIPTION OF THE DRAWINGS

The above and other features and advantages of the present invention will become apparent in the following detailed description of the preferred embodiments with reference to the accompanying drawing, of which.

DETAILED DESCRIPTION OF THE INVENTION

Figure 1:
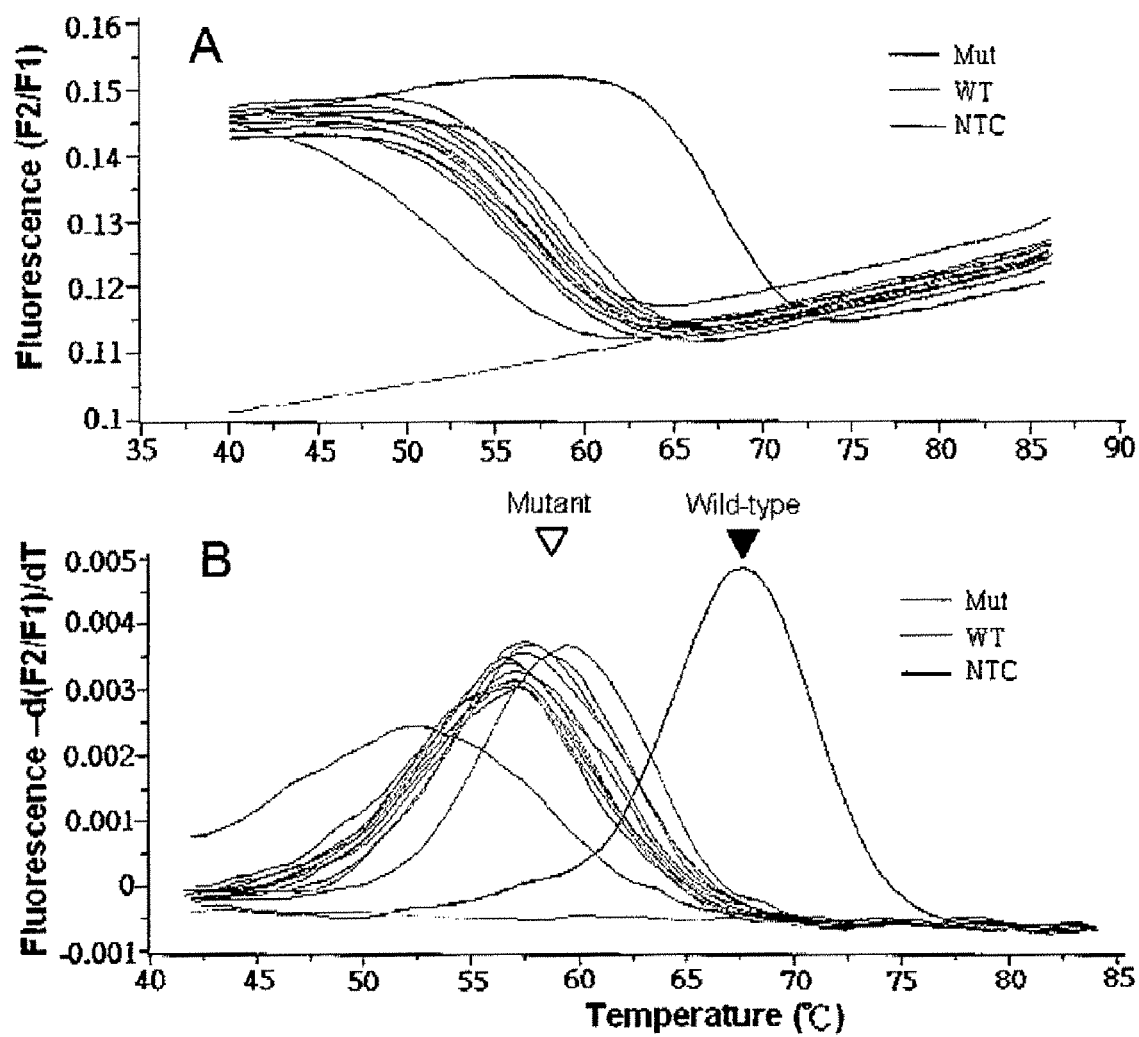
FIG. 1 shows that a 17-mer PNA sensor probe as prepared in the Examples, infra, differentiates 12 possible K-ras mutations in codons 12 and 13 from the wild-type K-ras, wherein 12 mutant templates generated by PCR-mediated site-directed mutagenesis were used to test the resolution of the PNA sensor probe, and all the PCR were performed under non-clamping conditions using primers F1 and R (see Table 1, infra) and 72° C. for extension. Melting curves (panel A) and melting peaks (panel B) were plotted after PCR Filled and open arrowheads indicate wild-type and mutant melting peaks, respectively. Abbreviations: Mut, mutant templates; WT, wild-type templates; NTC, no template control.

For the purpose of this specification, it will be clearly understood that the word "comprising" means "including but not limited to", and that the word "comprises" has a corresponding meaning.

It is to be understood that, if any prior art publication is referred to herein, such reference does not constitute an admission that the publication forms a part of the common general knowledge in the art, in Taiwan or any other country.

Unless otherwise defined, all technical and scientific terms used herein have the meaning commonly understood by a person skilled in the art to which this invention belongs. One skilled in the art will recognize many methods and materials similar or equivalent to those described herein, which could be used in the practice of the present invention. Indeed, the present invention is in no way limited to the methods and materials described. For clarity, the following definitions are used herein.

As used herein, the term "nucleotide sequence" refers to either a homopolymer or a heteropolymer of deoxyribonucleotides, ribonucleotides or other nucleic acids. As used herein, the term "nucleotide" generally refers to the monomer components of nucleotide sequences even though the monomers may be nucleoside and/or nucleotide analogs, and/or modified nucleosides such as amino modified nucleosides in addition to nucleotides. In addition, "nucleotide" includes non-naturally occurring analog structures. Thus, for example, the individual units of a peptide nucleic acid, each containing a base, are referred to herein as a nucleotide.

As used herein, the term "nucleic acid" refers to at least two nucleotides covalently linked together. A nucleic acid of the present invention will generally contain phosphodiester bonds, although in some cases nucleic acid analogs are included that may have alternate backbones, comprising, e.g., phosphoramides, phosphorothioate, phosphorodithioate, O-methylphosphoroamidite linkages, and peptide nucleic acid backbones and linkages. Other nucleic acid analogs include those with positive backbones, non-ionic backbones and non-ribose backbones. Nucleic acids may be single-stranded or double-stranded, as specified, or contain portions of both double-stranded or single-stranded sequence. The nucleic acid may be DNA, both genomic and cDNA, RNA or DNA-RNA hybrids where the nucleic acid contains any combination of deoxyribo- and ribo-nucleotides, and any combination of bases, including uracil, adenine, thymine, cytosine, guanine, inosine, xathanine, hypoxathanine, etc. Reference to a "DNA sequence" can include both single-stranded and double-stranded DNA. A specific sequence, unless the context indicates otherwise, refers to the single strand DNA of such sequence, the duplex of such sequence with its complement (double stranded DNA) and/or the complement of such sequence.

As used herein, the term "DNA fragment" refers to a DNA polymer, in the form of a separate segment or as a component of a larger DNA construct, which has been derived either from isolated DNA or synthesized chemically or enzymatically such as by methods disclosed elsewhere herein.

As used herein, the term "nucleic acid sample" refers to a sample containing nucleic acid molecules of various lengths, such as genomic DNA, mitochondrial DNA, cDNA, mRNA, plasmid, cosmid, yeast artificial chromosomes, artificial or man-made polynucleotides.

As used herein, the term "complementary" refers to the ability of two nucleotide sequences to bind sequence-specifically to each other by hydrogen bonding through their purine and/or pyrimidine bases according to the usual Watson-Crick rules for forming duplex nucleic acid complexes. It can also refer to the ability of nucleotide sequences that may include modified nucleotides or analogues of deoxyribonucleotides and ribonucleotides to bind sequence-specifically to each other by other than the usual Watson Crick rules to form alternative nucleic acid duplex structures.

As used herein, the term "hybridization" refers to the process by which two nucleotide sequences complementary to each other bind together to form a duplex sequence or segment.

As used herein, the term "duplex" refers to a structure formed as a result of hybridization of two complementary sequences of nucleic acids. Such duplexes can be formed by the complementary binding of two DNA segments to each other, two RNA segments to each other, or of a DNA segment to an RNA segment, the latter structure being termed as a hybrid duplex. Either or both members of such duplexes can contain modified nucleotides and/or nucleotide analogues as well as nucleoside analogues. As disclosed herein, such duplexes are formed as the result of binding of one or more probes to a sample sequence, such as PNA/DNA complex formed according to the processes of this invention.

As used herein, the term "wild-type polynucleotide" refers to a polynucleotide having a nucleotide sequence that is considered to be normal or unaltered. The term "wild-type polynucleotide" may be used interchangeably with the term "wild-type DNA" or "wild-type template."

As used herein, the term "mutant polynucleotide" refers to a polynucleotide having a nucleotide sequence that is different from the nucleotide sequence of the corresponding wild-type polynucleotide. The difference in the nucleotide sequence of the mutant polynucleotide as compared to the wild-type polynucleotide is referred to as the nucleotide "mutation" or "variation." The term "nucleotide variation" refers to one or more nucleotide substitution, deletion, insertion and/or modification changes.

As used herein, the terms "a target polynucleotide" and "target sequence" and the like refer to a specific polynucleotide sequence that is the subject of hybridization with a complementary polynucleotide, e.g., a blocking oligomer, or the subject of primer extension process. The target sequence can be composed of DNA, RNA, analogs thereof, or combinations thereof. The target sequence can be single-stranded or double-stranded. In primer extension processes, the target polynucleotide which forms a hybridization duplex with the primer may also be referred to as a "template." A template serves as a pattern for the synthesis of a complementary polynucleotide. A target sequence for use with the present invention may be derived from any living or once living organism, including but not limited to prokaryotes, eukaryotes, plants, animals, and viruses, as well as synthetic and/or recombinant target sequences.

As used herein, the terms "selected region" and "variable region" are interchangeable and refer to a specific region of a target polynucleotide that is suspected to have nucleotide variation(s).

The term "polymerase chain reaction (PCR)" or "PCR process" refers to a method for amplifying a target polynucleotide based on repeated cycles of denaturation, primer annealing and extension reaction.

The term "primer" as used herein refers to an oligonucleotide of defined sequence that is designed to hybridize with a complementary, primer-specific portion of a target polynucleotide sequence and undergo primer extension. The primer can function as the starting point for the enzymatic polymerization of nucleotides. The primer should be long enough to prevent annealing to sequences other than the complementary portion. Generally, the primer is between 10 to 50 nucleotides in length. Preferably, the primer is between 13 to 30 nucleotides in length.

The term "probe" as used herein refers to an oligonucleotide that is capable of forming a duplex structure by complementary base pairing with a sequence of a target polynucleotide and is generally not able to form primer extension products. The terms "peptide nucleic acid probe" and "detectable peptide nucleic acid probe" are used interchangeably and refer to a peptide nucleic acid labeled with a detectable moiety which can be detected directly or indirectly by virtue of generating a signal.

The term "extension reaction" as used herein refers to a template-dependent polymerization of a polynucleotide included in a PCR process as known in the art. According to this invention, the term "extension" may be used interchangeably with the term "elongation."

As used herein, the term "$T_m$" is used in reference to the "melting temperature." The melting temperature is the temperature at which a population of double-stranded polynucleotide molecules or nucleobase oligomers, in homoduplexes or heteroduplexes, become half dissociated into single strands. The equation for calculating the $T_m$ between two molecules takes into account the base sequence as well as other factors including structural and sequence characteristics and nature of the oligomeric linkages.

The melting temperature can be obtained in many ways. For example, the melting temperature can be theoretically determined based on the base length of a PNA-DNA duplex, and a mismatch in the duplex will result in a decrease of $T_m$ by about 10-18° C. (E. M. Kyger et al. (1998), *Anal. Biochem.*, 260, 142-148) However, the $T_m$ of a duplex is usually determined experimentally by subjecting a sample of duplexes to a constitutive increase in temperature and continuously measuring the dissociation of duplexes into single strands. Methods for determining $T_m$ are well known in the art. For example, $T_m$ may be determined by a shift in UV absorbance, by Surface Plasmon Resonance (SPR), or preferably by fluorescence.

The melting temperature predominantly depends on the size of the double stranded region of the probe/target polynucleotide duplex. In case a probe comprising repetitive sequences is used, the temperature for annealing thus depends on and can be correlated with the number of repetitions present in the target polynucleotide. In addition, it is known in the art and should not be neglected, that the melting temperature also depends on the GC-content of the double stranded region, the presence or absence of mismatches within the double stranded region, and other factors.

The term "melting analysis" or "melting curve analysis" as used herein refers to a procedure for analyzing the melting temperatures of amplified PCR products generated from the cycling profile of a PCR process.

Detection of rare mutant DNA from a background of wild-type alleles is important but sometimes difficult in the laboratory. Such rare mutations are commonly found in a cancer-related gene, a mitochondrial gene at a low heteroplasmic frequency, or a gene from a small subpopulation of bacteria or viruses, for example. They may only consist of a single change in the DNA sequence (e.g., a point mutation) and usually exist in very low abundance in the samples compared with the wild type. Therefore, assays to detect such mutant DNA must be very specific and sensitive. In addition, if mutations are identified as useful markers, a simple and rapid method for their detection is needed to facilitate the screening of a large number of samples.

Conventional methods to enrich the mutant signal include allele-specific amplification (H. linuma et al. (2000), *Int. J. Cancer*, 89-337-344), sequence specific ligation (D. A. Nickerson et al. (1990), *Proc. Natl. Acad. Sci., USA* 87:8923-8927), and restriction enzyme digestion of wild type DNA (C. P. Dieterle et al. (2004), *Clin. Cancer Res.*, 10:641-650; Jacobson, D. R. & Mills, N. E. (1994), *Oncogene*, 9:553-563; Norheim Andersen, S. et al. (1996), *Br. J. Cancer*, 74:99-108). These methods usually require subsequent detection procedures, such as gel electrophoresis (T. Nishikawa et al. (2002), *Clin. Chim. Acta*, 318:107-112; S. Toyooka et al. (2003), *Oncol. Rep.*, 10:1455-1459; M. Imai et al. (1994), *Cancer*, 73:2727-2733), hybridization (M. Maekawa et al. (2004), *Clin. Chem.*, 50:1322-1327), mass-spectrometry (M. E. Lleonart et al. (2004), *Nucleic Acids Res.*, 32, e53; X. Sun et al. (2002), *Nat. Biotechnol.*, 20:186-189), or denaturing high-performance liquid chromatography (S. L. Lilleberg et al. (2004), *Ann. N Y Acad. Sci.*, 1022:250-256), which can be laborious and increase the risk of contamination.

The use of fluorescent probes and melting curve analysis for genotyping was first introduced by Lay, et al. (Lay, M. J. & Wittwer, C T. (1997), *Clin. Chem.*, 43:2262-2267) and was soon modified to include a pair of hybridization probes (P. S. Bernard et al. (1998), *Am. J. Pathol.*, 153:1055-1061). The probes, namely a sensor and an anchor, are two oligonucleotides labeled with different fluorophores between which fluorescence resonance energy transfer (FRET) can occur. When these two fluorophores are close to each other, one of them (the donor) absorbs excitation light and transfers energy to the other fluorophore (the acceptor), which in turn emits a specific wavelength of light. This acceptor emission reveals the status of probe binding because FRET only occurs when these two probes anneal to adjacent sites of a complementary DNA strand.

Conventionally, a longer probe with higher melting temperature ($T_m$) serves as an anchor because R remains annealed to the complementary DNA at temperatures which cause the dissociation of a shorter probe that has a lower $T_m$. Monitoring the acceptor emission generated by FRET along with temperature change produces a melting curve which displays the interaction between probes and the complementary DNA. Because the shorter probe dissociates from the complementary DNA first, resulting in a drop in the intensity of the acceptor emission, the melting curve profile actually reveals behavior of the shorter probe. When the shorter probe is positioned over the variable region, it serves as a sensor because any change of DNA sequence in this region results in a shift in its $T_m$, altering the melting curve profile.

Today, a combination of real-time PCR and hybridization probes has become a powerful tool for the detection of single nucleotide polymorphisms (SNP) causing inherited diseases (M. Rodriguez-Manotas et al. (2006), *Clin. Chim. Acta*, 364: 343-344; M. Heesen et al. (2003), *Clin. Chim Acta*, 333, 47-49; J. Popp et al. (2003), *Pharmacogenomics*, 4-643-646). Genotyping SNPs responsible for inherited diseases using hybridization probes is easy, as these kinds of sequence variations can comprise up to 50% (if the mutation is heterozygous) or even 100% (in the case of a homozygous mutation) of the total alleles present. However, applying hybridization probes to the detection of somatic mutations in clinical samples (the most frequently observed of which occur in cancer cells, such as the K-ras or p53 mutations) can be difficult, because the wild-type alleles from normal cells usually account for the majority of DNA and only relatively small amounts of mutant alleles exist. The wild-type template can exhaust essential reagents during PCR, and its product will mask the mutant signal during melting curve analysis. Conventional methods to enrich the mutant PCR products, such as restriction enzyme digestion or sequence specific primer extension, are not compatible with hybridization probes as they need a PCR primer that extends to the variable region of the template, which will compete with a probe that binds to the same region.

The addition of a PNA clamp into a PCR that contains a pair of hybridization probes (K. A. Kreuzer et al. (2003), *Ann. Hematol.*, 82; 284-289; C. Y Chen et al (2004), *Clin Chem* 50, 481-489; J. Dabritz et al. (2005), *J. Cancer*, 92:405-412) or hydrolysis probes (also known as TaqMan probes) (Y. Nagai et al. (2005), *Cancer Res* 65:7276-7282) allows homogeneous detection of rare mutant DNA in a closed tube. However, in such designs, the added PNA competes for DNA binding with the sensor probe. The sensor probe therefore should be mutation-specific, i.e., it complements one of the mutant alleles instead of the wild-type allele. Some researchers introduced a DNA analog, the locked nucleic acid (LNA), as the mutation-specific probes for better competition with the PNA clamp (LNA probes have a higher affinity and better discrimination between wild-type and mutant templates than DNA probes) (Y. Nagai et al. (2005), supra). The mutation-specific probe allows the mutation type to be determined, as it correlates to the specific probe sequence. However, the disadvantage is that if more than one type of mutation occurs in the target region, several probes would need to be synthesized and tested for their efficiency and compatibility when combined in the same reaction.

In a previous study, the Applicants developed a simple method to detect trace amounts of K-ras mutants by using PNA as both PCR clamp and hybridization probe in a capillary PCR reaction (Chiuan-Chian Chiou and Ji-Dung Luo, Detection of Trace Amounts of Mutant K-ras DNA by Peptide Nucleic Acid as Both PCR Clamp and Sensor Probe, Poster Session Abstracts of The San Diego Conference Cool Tools and Hot Applications Nov. 18-20, 2004 San Francisco, Calif.). However, this method has the disadvantages of poor sensitivity and reproducibility.

Therefore, in this invention, the applicants provide a method for determining whether a target polynucleotide sequence contained in a nucleic acid sample has nucleotide variation(s) in a selected region thereof, comprising the steps of:

providing a pair of a first primer and a second primer which allows the formation of a PCR product having a sequence covering that of the selected region of the target polynucleotide sequence via a PCR process, the first primer having a sequence identical to that of a first region located upstream of the selected region of the target polynucleotide sequence, the second primer having a sequence based on that of a second region located downstream of the selected region of the target polynucleotide sequence, wherein the 5'-end of the sequence of the first region is spaced apart from the 5'-end of the sequence of the sequence of the selected region by 30 nucleotides or more;

providing a detectable peptide nucleic acid probe having a sequence that complements fully the sequence of the selected region of the target polynucleotide sequence having no nucleotide variation(s) therein, such that hybridization of the detectable peptide nucleic acid probe to the selected region of the target polynucleotide sequence having no nucleotide variation(s) results in the formation of a duplex having a melting temperature;

determining the melting temperature of the duplex;

admixing the detectable peptide nucleic acid probe and the pair of the first primer and the second primer with the nucleic acid sample to form a mixture;

subjecting the mixture to a PCR process including an extension reaction set to run at a temperature lower than the melting temperature of the duplex by 5 to 20° C., such that a mixture of PCR products is obtained; and subjecting the mixture of PCR products thus obtained to a melting analysis to determine melting temperatures of the PCR products, wherein the presence of at least one melting temperature lower than the melting temperature of the duplex is indicative of the nucleotide variation(s) in the selected region of the target polynucleotide sequence contained in the nucleic acid sample.

According to this invention, the nucleic acid sample may be obtained from an organism selected from viruses, bacteria, fungi, plants, and animals. Preferably, the nucleic acid sample is obtained from a mammal. In a preferred embodiment of this invention, the mammal is human.

According to this invention, the nucleic acid sample can be obtained from a specimen of body fluid or tissue biopsy of a subject, or from cultured cells. The body fluid may be selected from whole blood, serum, plasma, urine, sputum, bile, stool, bone marrow, lymph, semen, breast exudate, bile, saliva, tears, bronchial washings, gastric washings, spinal fluids, synovial fluids, peritoneal fluids, pleural effusions, and amniotic fluid.

According to this invention, the target polynucleotide sequence comprises a gene selected from the group consisting of disorder-associated gene, drug-resistance gene and virulence gene.

According to this invention, the disorder-associated gene may include, but is not limited to: cancer-associated genes and genes associated with a hereditary disease.

According to this invention, the cancer-associated gene may include, but is not limited to: K-ras, H-ras, N-ras, p53 (TP53), CDKN2A (p16), PIC3K, PTEN, RB1, epidermal growth factor receptor gene, BRAF, BRCA1, BRCA2, STK11, and VHL. In a preferred embodiment of this invention, the cancer-associated gene is K-ras.

According to this invention, the hereditary disease includes maternally inherited disorders due to mutations in mitochondrial DNA. Examples of genes associated with a hereditary disease include, but are not limited to: NF1, FBN1, MSH2, MLH1 (autosomal dominant disorder-associated gene); CFTR, Hemoglobin beta gene, HEXA, SMN1, VAPB (autosomal recessive disorder-associated gene); PHEX (X-linked dominant disorder-associated gene); factor VIII, dystrophin gene, CNGA 3, CNGB3, GNAT2, androgen receptor (AR) gene (X-linked recessive disorder-associated gene); USP9Y (Y-linked disorder-associated gene); MT-ND1, MT-ND4, MT-ND4L, MT-ND6 (mitochondrial disease-associated gene).

As used herein, the term "drug-resistance gene" refers to genes encoding the factors that govern the responsiveness to a drug for treatment. The drug-resistance genes may include, for example, the epithelial growth factor receptor (EGFR) gene which encodes EGFR in respect to the drug (gefitnib) for treatment of lung cancer, the multi-drug resistance-associated protein (MRP) gene encoding MRP in respect to the drug for treatment of ovarian cancer, and the lung resistance protein (LRP) gene in respect to the drug for treatment of ovarian cancer.

As used herein, the term "virulence gene" refers to genes encoding virulence factors from any pathogenic organism (e.g., bacteria, protists, yeast, fungi, etc.). The virulence genes may include, but are not limited to: cagPAI, vacA, iceA, babA, erp, spvC, spuB, cnf1, cnf2, eaeA, eagg, einv, stx1, stx2, and vt2e, Examples of pathogenic organisms include *Yersinia pestis, Pseudomonas aeruginosa, Neisseria meningitides* serogroup A and B, *Helicobacter pylori, Chlamydia trachomatis, Chlamydia pneumoniae, Streptococcus pneumoniae, Haemophilus influenzae, Mycobacterium leprae, Mycobacterium tuberculosis, Vibrio cholerae, Staphylococcus aureus, Giardia lamblia, Escherichia coli, Entamoeba histolytica, Trichomonas vaginalis, Leishmania donovani, Trypannosome cruzi, Candida albicans, Plasmodium falciparum*, etc.

According to this invention, the nucleotide variation(s) in the selected region of the target polynucleotide sequence may include one or more nucleotide substitution, deletion, insertions and/or abnormal methylation.

In higher order eukaryotes, DNA is methylated only at cytisines located 5' to guanosines in the CpG dinucleotides (R. Holliday and G. W. Grigg (1993), *Mutat. Res.*, 285: 6167). This modification has important regulatory effects on gene expression, especially when involving CpG-rich areas known as CpG islands, located in the promoter regions of many genes (A. Bird, (1992), *Cell,* 70: 5-8, A. P. Bird (1986), *Nature*, 321; 209-213).

Methylation of promoter CpG islands is associated with histone deacetylation and transcriptional silencing (P. A. Jones (1999), *Nat. Genet.*, 21: 163-167) and is essential for normal embryonic development, genomic imprinting, and X-chromosome inactivation. Somatic de novo methylation of CpG islands in tumor suppressor genes has been implicated in tumorigenesis, and aberrant methylation of imprinted genes is associated with several inherited human diseases (P. A. Jones (1999), *Nat. Genet*, 21: 163-167; S. B. Baylin et al. (1998), *Adv. Cancer Res,* 72: 141-196; A. P. Feinberg (2000), *Curr. Top Microbiol. Immunol.*, 249-87-99). Detection of methylation in CpG islands has become an important tool for understanding both normal and pathologic gene expression events.

According to this invention, in order to detect the presence of any abnormal methylation in the target polynucleotide, a preliminary treatment should be conducted prior to the practice of the present method. Specifically, the nucleic acid sample should be chemically modified by a bisulfite treatment, which will convert cytosine to uracil but not the methylated cytosine (i.e., 5-methylcytosine, which is resistant to this treatment and remains as cytosine) (R. Y. H., Wang et al. (1980), *Nucleic Acids Res.*, 8, 4777-4790). In addition, the PNA probe should be designed based on the sequence of the bisulfite-treated wild-type DNA. With these modifications, the method of this invention can be applied to the detection of abnormal methylation(s) in the target polynucleotide.

The applicants found that the position of the primer having a sequence identical to that of a region located upstream of the selected region of the target polynucleotide sequence affected the efficiency of PCR clamping. Therefore, according to the method of this invention, the 5'-end of the sequence of the first region is preferably spaced apart from the 5'-end of the sequence of the selected region by 30 to 2000 nucleotides. More preferably, the 58-end of the sequence of the first region is spaced apart from the 5'-end of the sequence of the selected region by 50 to 1500 nucleotides. More preferably, the 5'-end of the sequence of the first region is spaced apart from the 5'-end of the sequence of the selected region by 50 to 1000 nucleotides. More preferably, the 5'-end of the sequence of the first region is spaced apart from the 5'-end of the sequence of the selected region by 50 to 500 nucleotides. More preferably, the 5'-end of the sequence of the first region is spaced apart from the 5'-end of the sequence of the selected region by 50 to 200 nucleotides. In a preferred embodiment of this invention, the 5'-end of the sequence of the first region is spaced apart from the 5'-end of the sequence of the selected region by 121 nucleotides. In another preferred embodiment of this invention, the 5' end of the sequence of the first region is spaced apart from the 5'-end of the sequence of the selected region by 97 nucleotides.

In addition to the position of the primer, the applicants found that the extension temperature set for the PCR process also had great influence on the efficiency of PCR clamping. According to this invention, the extension reaction is preferably set to run at a temperature lower than the melting temperature of the duplex of the PNA probe and the wild-type polynucleotide by 5 to 20° C., preferably 5 to 18° C. More preferably, the extension reaction is set to run at a temperature lower than the melting temperature of the duplex by 8 to 18° C. More preferably, the extension reaction is set to run at a temperature lower than the melting temperature of the duplex by 8 to 16° C. In a preferred embodiment, the extension reaction is set to run at a temperature lower than the melting temperature of the duplex by 9° C.

Figure 4:
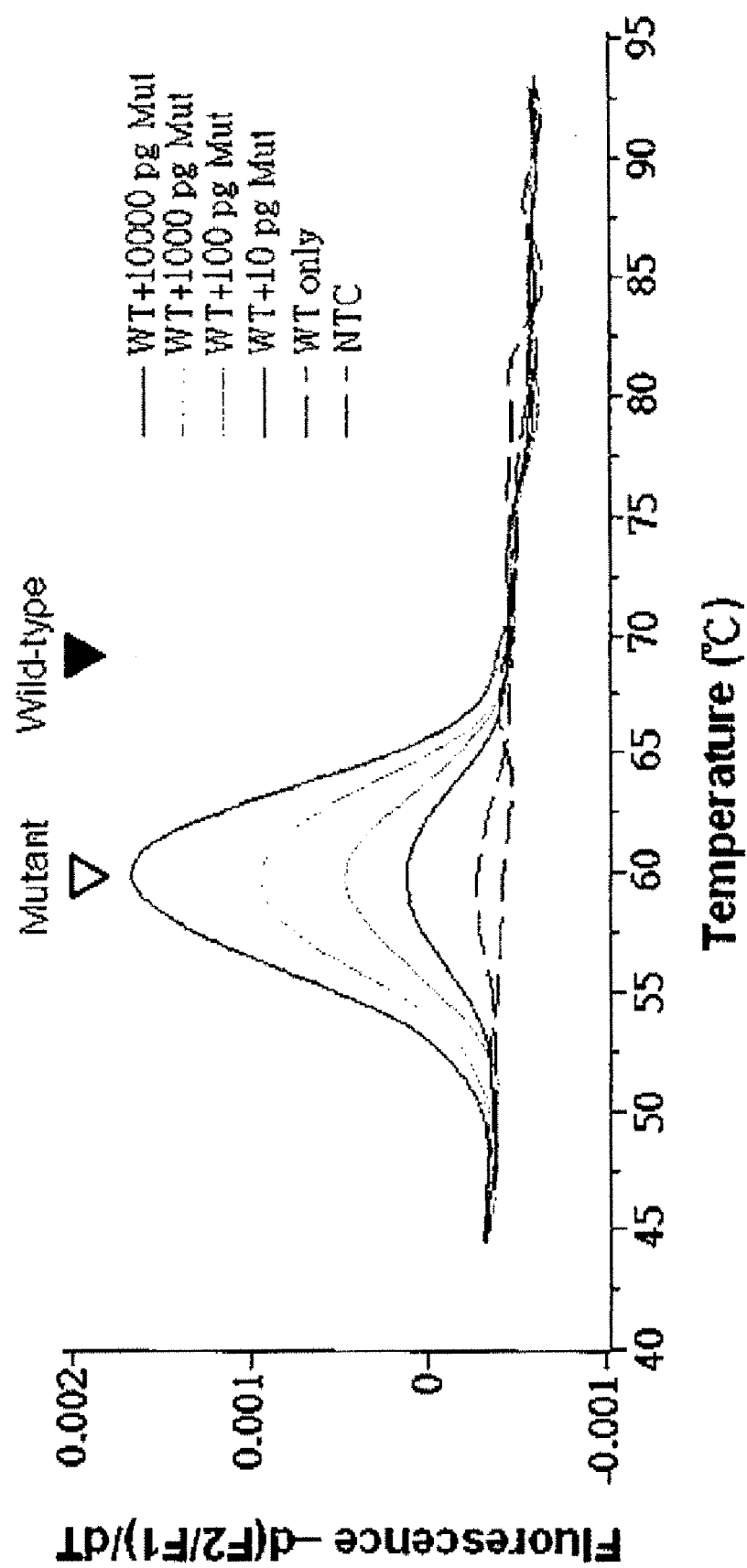
FIG. 4 shows the assay sensitivity for detection of rare K-ras mutants in a large excess of wild-type DNA, wherein 100 ng of wild-type templates plus various amounts of mutant templates were used for PNA-clamping PCR. Under the optimal condition using F2 as the forward primer and 60° C. as extension temperature, the assay detected the signal from as few as 10 pg mutant templates without interference from the wild-type templates. Filled and open arrowheads indicate wild-type and mutant melting peaks, respectively Abbreviations: WT, wild-type templates; Mut, mutant templates; and NTC, no template control.

Particularly, when the 5'-end of the sequence of the first region is spaced apart from the 5'-end of the sequence of the selected region by 97 nucleotides, and the extension reaction is set to run at a temperature lower than the melting temperature of the duplex by 9° C., the method of this invention can detect as low as 10 pg of mutant DNA against a background of 100 ng of wild-type DNA (1:10000 ratio) (see FIG. 4).

Using the method of this invention, the applicants were able to detect 19 mutants in a group of 24 serum samples obtained from patients with pancreatic cancer (see Table 2, infra). The result suggests that the method of this invention can serve as a useful tool for cancer screening as well as in the detection of rare mutation(s) in many diseases.

According to this invention, the detectable PNA probe has several advantages over DNA probes (E. M. Kyger et al. (1998), supra). First, PNA-DNA hybrids are more stable than DNA-DNA hybrids. Second, sodium concentrations are less influential in the hybridization kinetics of PNA. Third, the detectable PNA probes are more sensitive to internal base pair mismatches with their DNA complement. Finally, PNA rarely serve as primers for DNA polymerases.

Methods for the design of PNA are well known to those skilled in the art (See, e.g. Applied Biosystems website under Technical Tools "PNA Probe Designer"). The length and the sequence of the detectable PNA probe used in this invention may be designed depending on the requirement of different experimental conditions. The synthesis of the PNA is also detailed in various publications, including Hyrup and Nielsen (1996), Bioorg Med. Chem., 4: 5-23; WO 92/20702; WO 92/20703 and U.S. Pat. No. 5,539,082, the contents of which are incorporated herein by reference. In a preferred embodiment of this invention, the detectable PNA probe ranges from 8 to 30 mer in length.

According to this invention, the detectable PNA probe may be labeled with a fluorescent moiety, a photoluminescent moiety, a luminescent moiety, or a chemiluminescent moiety.

In a preferred embodiment of this invention, the detectable PNA probe is labeled with a fluorescent moiety. Examples of suitable fluorescent moieties include fluorescein, rhodamine, FAM, TET, HEX, JOE, TAMA, NTB, TAMRA, ROX, VIC, NED, 4,7-dichloro-fluorescein, 4,7-dichloro-rhodamine, Cy5, Cy3, Texas Red, DABCYL, DABSYL, malachite green, cyanine, LC-Red610, LC-Red640, LC-Red670, LC-Red705, and derivatives thereof. In a more preferred embodiment of this invention, the fluorescent moiety is fluorescein.

As a variant, the detectable PNA probe can be designed to form a hairpin stem-loop molecular beacon, wherein the PNA itself constitutes the loop structure. Details of preparation of molecular beacons can be found in various literature and patent publications, see, e.g. U.S. Pat. No. 7,081,336 B2 and G. K. Leondios et al. (1998), science, 279:1228-1229.

In addition, according to this invention, an anchor probe may be additionally added in the admixing step. When the detectable PNA probe and the anchor probe are labeled with different fluorophores (e.g. fluorescein versus LC-Red 640), fluorescence resonance energy transfer (FRET) can occur between the detectable PNA probe and the anchor probe. Specifically, when the two fluorophores are close to each other, one of them (the donor) absorbs excitation light and transfers energy to the other fluorophore (the acceptor), which in turn emits a specific wavelength of light. This acceptor emission reveals the status of probe binding because FRET only occurs when these two probes anneal to adjacent sites of a complementary DNA strand.

According to this invention, the anchor probe may be labeled with a fluorescent dye, including, but not limited to: fluorescein, rhodamine, FAM, TET, HEX, JOE, TAMA, NTB, TAMRA, ROX, VIC, NED, 4,7-dichloro-fluorescein, 4,7-dichloro-rhodamine, Cy5, Cy3, Texas Red, DABCYL, DABSYL, malachite green, cyanine, LC-Red610, LC-Red640, LC-Red670, LC-Red705, and derivatives thereof. In a preferred embodiment of this invention, the anchor probe is labeled with fluorescent LC-Red 640.

According to this invention, there is also provided a kit for determining whether a target polynucleotide sequence contained in a nucleic acid sample has nucleotide variation(s) in a selected region thereof, comprising:

a detectable peptide nucleic acid probe having a sequence that complements fully the sequence of the selected region of the target polynucleotide sequence having no nucleotide variation(s) therein, such that hybridization of the detectable peptide nucleic acid probe to the selected region of the target polynucleotide sequence having no nucleotide variation(s) results in the formation of a duplex having a melting temperature;

a pair of a first primer and a second primer which allows the formation of a PCR product having a sequence covering that of the selected region of the target polynucleotide sequence via a PCR process, the first primer having a sequence identical to that of a first region located upstream of the selected region of the target polynucleotide sequence, the second primer having a sequence based on that of a second region located downstream of the selected region of the target polynucleotide sequence, wherein the 5'-end of the sequence of the first region is spaced apart from the 5'-end of the sequence of the selected region by 30 nucleotides or more; and an instruction sheet providing guidance for a user to use the detectable peptide nucleic acid probe and the pair of the first primer and the second primer in a manner as defined in the aforesaid method for determining whether a target polynucleotide sequence contained in a nucleic acid sample has nucleotide variations in a selected region thereof.

The method and kit of this invention are very useful in the detection of rare alleles at "hotspots" of sequence variation. In addition, it is contemplated that the method and kit of this invention can be performed in one or more capillary tubes or on one or more microarrays or biochips, thereby allowing the detection of plural selected regions in a target gene at one time.

This invention will be further described by way of the following examples. However, it should be understood that the following examples are solely intended for the purpose of illustration and should not be construed as limiting the invention in practice.

EXAMPLES

Materials and Methods

1. Primers and Probes:

For PCR, three forward primers (F1, F2 and F3) and a reverse primer (R) were designed based on the genomic sequence of K-ras exon 1 so as to amplify DNA fragments containing the variable (selected) region of the K-ras gene [NCBI Accession Number L00045 (Locus: HUMRASK02)] of interest.

A sensor probe having a sequence that complements fully the sequence of the variable region of wild-type K-ras gene, was designed to be a 17-mer PNA labeled with fluorescein at its N-terminal (equivalent to the 5'-end of a DNA oligomer) via an O-linker. An anchor probe was designed to be a 44mer DNA labeled with fluorescent dye LC-Red 640 at the 3'-end thereof. The PCR primers and the anchor probe were provided by TIB MOLBIOL (Berlin, Germany). The PNA probe was provided by Applied Biosystems (Forster City, Calif., USA). Sequences of primers and probes used in the following experiments are listed in Table 1.

mini kit (Qiagen, Hilden, Germany) Purified DNA was quantified by ultraviolet (UV) spectrophotometry and stored at −20° C. until use.

Mutant templates were either purified from cell line SW480 (BCRC60249, obtained from Bioesource Collection and Research Center (BCRC), Hsinchu, Taiwan) using the QIAamp DNA-blood-mini kit, or synthesized by PCR-based site-directed mutagenesis. The SW480 cells harbor a G to T mutation at the second base of codon 12 in the K-ras gene. The PCR-based site-directed mutagenesis was performed based on the wild-type K-ras template using one of 12 different primers complementary to the variable region of the K-ras gene but bearing a mismatch at either the first or second position of codon 12 or 13 (see Table 1). Sequences of all the synthesized mutant templates were verified by an autosequencer (ABI PRISM 377, Applied Biosystems, Foster City, Calif., USA). Thereafter, the synthesized mutant templates were purified using a QIAquick PCR purification kit (Qiagen, Hilden, Germany) and diluted with 10 mM Tris-HCl (pH 8.0) containing 1 µg/mL salmon sperm DNA and stored at −20° C. before use.

TABLE 1

Primers and probes used in the PCR experiments.

| Name | Sequence (5'-3' for DNA or N to C for PNA) | Positions[a] |
|---|---|---|
| Primers for site-directed mutagenesis | | |
| M1X[b] | atgactgaatataaacttgtggtagttggagctXgtggcgta (SEQ ID NO: 1) | 1~42 |
| M2X | atgactgaatataaacttgtggtagttggagctgXtggcgta (SEQ ID NO: 2) | 1~42 |
| M3X | atgactgaatataaacttgtggtagttggagctggtXgcgta (SEQ ID NO: 3) | 1~42 |
| M4X | atgactgaatataaacttgtggtagttggagctggtgXcgta (SEQ ID NO: 4) | 1~42 |
| PCR Primers | | |
| F1 | atgactgaatataaacttgtggta (SEQ ID NO: 6) | 1~24 |
| F2 | attaaccttatgtgtgacat (SEQ ID NO: 7) | −70~−51 |
| F3 | tactggtggagtatttgata (SEQ ID NO: 8) | −94~−75 |
| R | caagatttacctctattgtt (SEQ ID NO: 9) | 121~102 |
| Probes | | |
| PNA sensor probe | (Fluorescein)-cctacgccaccagctcc (SEQ ID NO: 10) | 44~28 |
| DNA anchor probe | gtccacaaaatgattctgaatgctgtatcgtcaaggcactct-(fluorescent dye LC-Red 640)(SEQ ID NO: 11) | 90~47 |

[a] A of the ATG start codon is designated as position 1.
[b] X represents either A, T or C. The number represents the position of four guanines in codons 12 and 13. Therefore, 'M1C' would indicate a G to C change at the first guanine.

2. Preparation of K-ras Templates:

Wild-type K-ras templates (genomic DNA) were purified from cultured human leukemia cell line K-562 (BCRC60007, obtained from Bioresource Collection and Research Center (BCRC), Hsinchu, Taiwan) using a QIAamp DNA-blood- 3. PCR Analysis:

PCR was performed in a 20 µL reaction mixture containing 1× reaction buffer [50 mM Tris (pH 8.5), 3 mM MgCl$_2$, 500 µg/mL BSA, deoxyrbonucleotide triphosphates (each 200 µM)] (Invitrogen, Carlsbad, Calif., USA), 0.5 µM forward and reverse primers, 0.25 µM PNA sensor probe, 0.2 µM DNA anchor probe, 0.5 U Platinum Taq (Invitrogen, Carlsbad, Calif., USA), and K-ras templates.

The amplification was performed on a LightCycler (Roche Diagnostics, Mannheim, Germany), starting with a 2 min denaturation at 94° C., then running for 50 cycles as follows. 94° C. held for 0 sec for denaturation; 70° C. held for 5 sec for PNA probe binding, 56° C. held for 0 sec for primer annealing, and 10 sec at various temperatures for extension. Melting analysis was performed after a 20 sec denaturation at 95° C. and then decreasing the temperature to 45° C. at a ramp rate of 0.7° C./sec. Detection of the amplified PCR products was made in channel F2 or F2/F1 for the LC-Red 640-labeled probe, 4. Detection of K-ras Mutation in Patients' Sera:

Serum samples were collected from 24 pancreatic cancer patients in Chang Gung Memorial Hospital, Taiwan. Control samples were collected from 10 healthy volunteers. DNA was extracted from 200 µL aliquots of serum using a QIAamp DNA-blood-mini kit (Qiagen). One-fourth of the eluted DNA was used as PCR template PCR was performed using F2 as the forward primer and 60° C. (clamp condition) or 72° C. (non-clamp condition) as extension temperature. Presumed mutants were identified as those samples having melting peaks close to 60° C. To confirm results and determine specific mutation types, PCR products were separated on a 2% agarose gel, eluted, and then sequenced by an automated DNA sequencer.

Results:

1. The 17-mer PNA Probe Differentiated Wild-Type K-ras from Mutants.

To determine whether the hybridization probes according to this invention could differentiate wild-type (genomic DNA of human leukemia cell line K-562) from mutant K-ras, the applicants made 12 mutant templates by PCR-based site-directed mutagenesis. The 12 mutant templates covered all possible single nucleotide mutations in codons 12 and 13 that result in amino acid changes. In the non-clamping PCR conditions using primers F1 and R and 72° C. for extension, all of these mutant templates as well as the wild-type template can be amplified. Melting curve analysis revealed that the $T_m$ of the PNA probe bound to wild-type K-ras is 69° C., but varies between 53 and 60° C. when bound to the different mutant templates (FIG. 1). This indicates that a single nucleotide change causes a $T_m$ shift of 9-16° C. for the 17-mer PNA probe.

2. The PNA Probe Suppresses PCR of Wild-Type Template but not of Mutant Templates at a Lower Extension Temperature.

Figure 2:
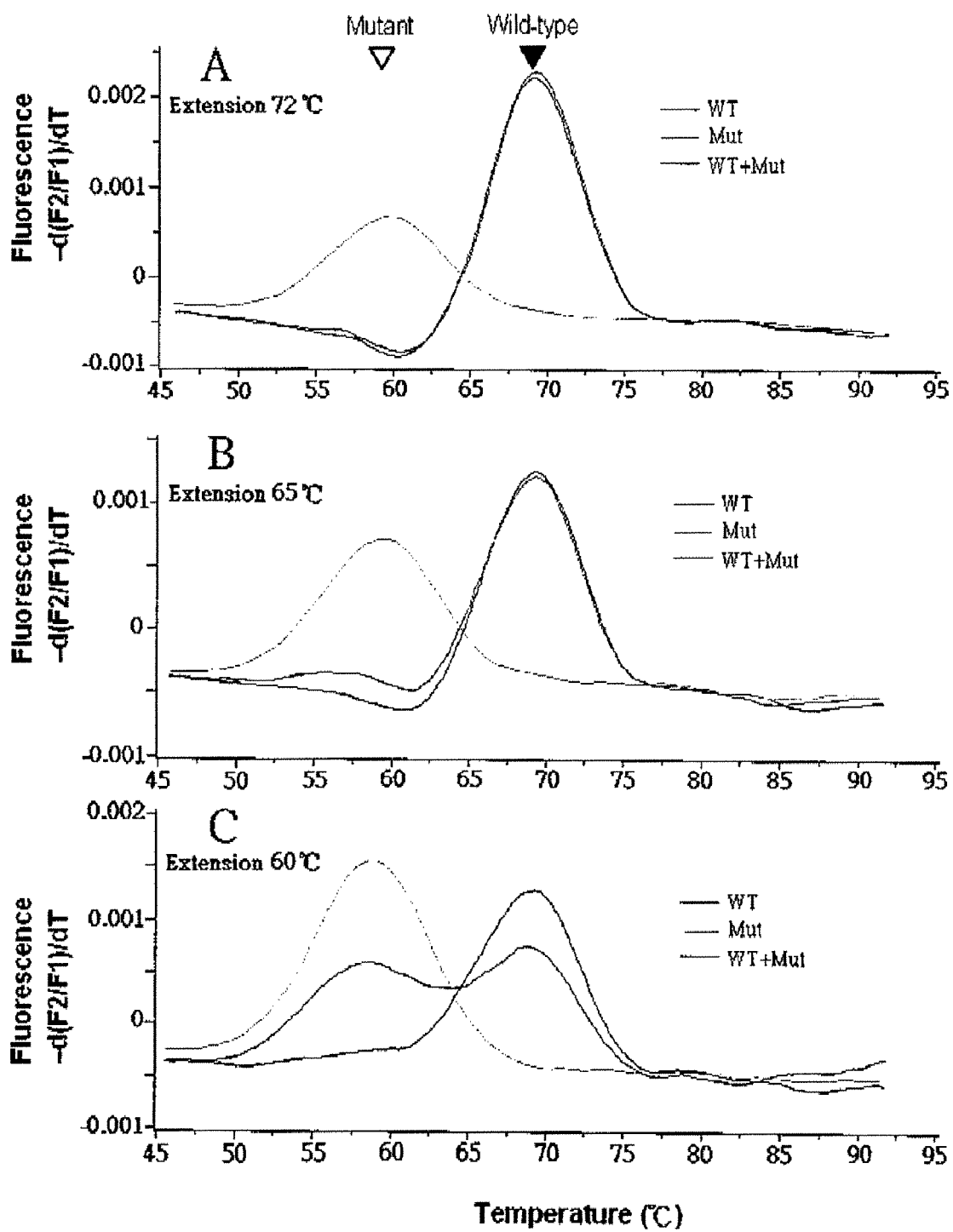
FIG. 2 shows that the efficiency of PNA-mediated PCR clamping is affected by different extension temperatures, wherein PCR were performed using either 100 ng wild-type templates (WT), 1 ng mutant templates (Mut), or a mix containing 100 ng wild-type and 1 ng mutant genomic DNA (WT+Mut) as templates and primer F1 as the forward primer. Extension temperatures were 72° C. (panel A), 65° C. (panel B) or 60° C. (panel C). Filled and open arrowheads indicate wild-type and mutant melting peaks, respectively.

To determine whether the conventional PCR extension step is conducted at a temperature that is too high for the PNA probe to inhibit elongation through the wild-type template, a mixture of 1 ng of mutant genomic DNA from cell line SW480 and a 100-fold excess of wild-type DNA was used as template for real-time PCR performed using primers F1 and R and different extension temperatures. When doing extension at 72° C. or 65° C., only the wild-type melting curve was seen, indicating that no obvious clamp occurred (FIG. 2, panels A and B). After lowering the extension temperature to 60° C., which is around the $T_m$ of the mutant templates and 9° C. lower than the wild-type $T_m$, the mutant peak started to appear (FIG. 2, panel C). A further decrease of the extension temperature to 55° C. or 50° C. slowed PCR amplification of both wild-type and mutant templates (data not shown).

3. Distant Primers Enhance PCR Clamping of Wild-Type Templates

Figure 3:
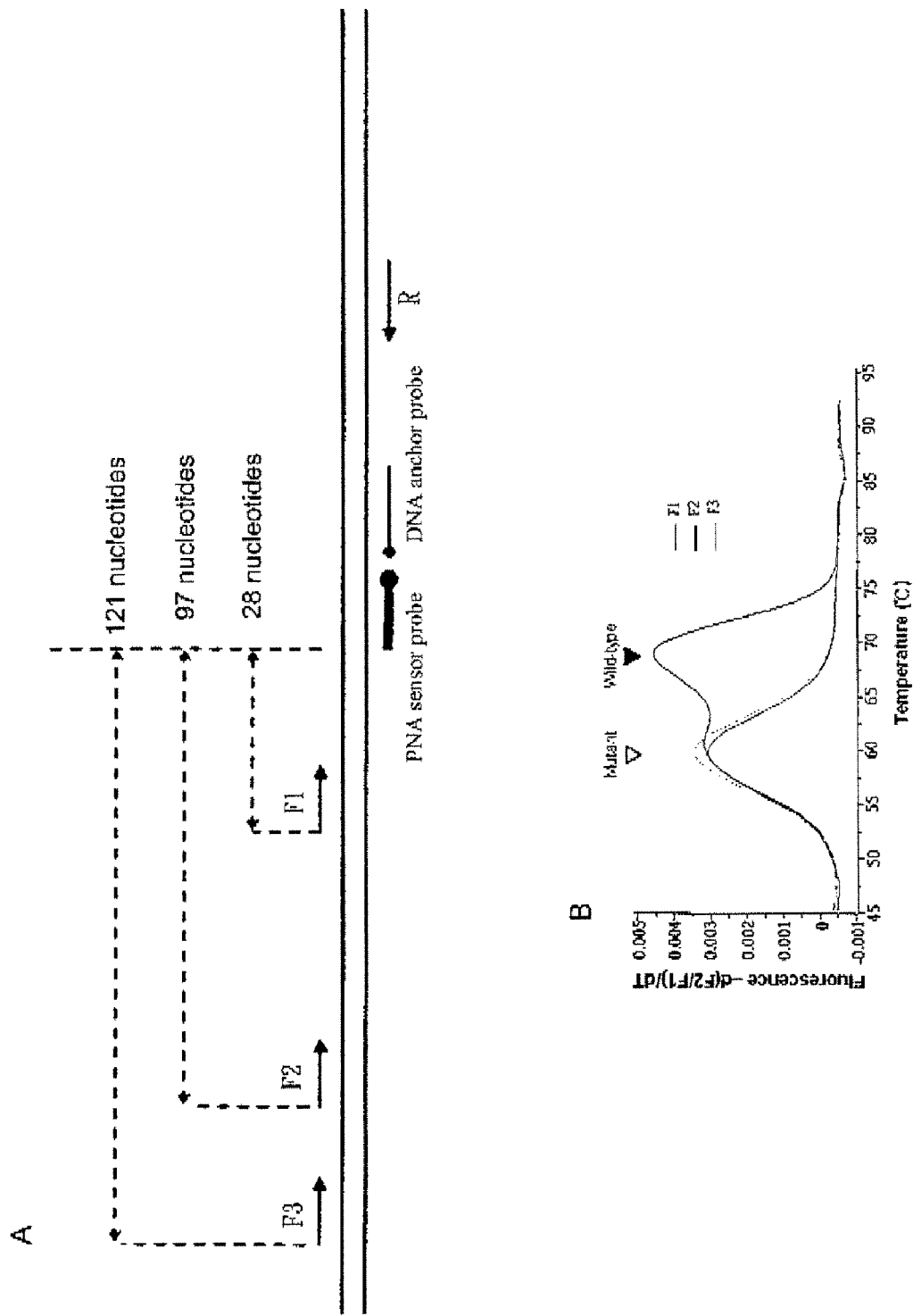
FIG. 3 shows that the efficiency of PNA-mediated PCR clamping is affected by the primer position, in which panel A shows relative positions and orientations of PCR primers, PNA probe and anchor probe, and panel B shows the melting peaks after PNA-clamping PCR using mixed templates containing 100 ng wild-type templates plus 1 ng mutant templates and either F1, F2 or F3 as the forward primer Filled and open arrowheads indicate wild-type and mutant melting peaks, respectively.

In addition to extension temperature, the applicants found that the priming position of the forward primer versus the PNA binding site also influences the PNA-mediated PCR clamping. When using primer F1, which primes a region of the K-ras gene upstream of the PNA binding site by 28-nt (FIG. 3, panel A), wild-type amplification could not be completely suppressed (see panel C of FIG. 2, and panel B of FIG. 3). However, when using primers F2 and F3, which prime a region of the K-ras gene upstream of the PNA binding site by 97-nt and 121-nt, respectively, amplification of the wild-type templates was successfully inhibited, and only the mutant templates were amplified (FIG. 3, panel B).

4. Detection of Rare Mutants in a Large Excess of Wild-Type DNA

To determine the present assay's limits for detecting rare mutants, the applicants used different amounts of mutant genomic DNA mixed with 100 ng of wild-type genomic DNA as templates. When performing PCR under optimal conditions using primers F2 and R and 60° C. for extension, as little as 10 pg of mutant DNA (about three genomes, or 1:10,000) was detected by melting curve analysis (FIG. 4).

5. Detection of K-ras Mutations in Serum DNA Data-:

Of 24 purified serum DNA samples from pancreatic cancer patients, 19 (79%) had melting peaks close to 60° C. and were presumed to be mutants; the other five samples without obvious peaks were presumed to be wild-type. Sequence analysis confirmed that each of the 19 "expected mutants" had a point mutation in codon 12 (Table 2). Note that samples of all the "expected wild-type," which could not be amplified during clamp-PCR, had been subjected to PCR under non-clamp condition to ensure that they contained amplifiable DNA (data not shown). In addition, using the present assay, all samples from the 10 healthy controls were determined to be wild-type (data not shown).

TABLE 2

Types of K-ras mutations found in the sera of the pancreatic cancer patients.

| Coden | mutation[a] | amino acid change | Number | Mutant melting peak |
|---|---|---|---|---|
| (12) | GGT → GTT | (Gly → Val) | 16 | Yes |
| (12) | GGT → AGT | (Gly → Ser1) | 1 | Yes |
| (12) | GGT → GAT | (Gly → Asp) | 1 | Yes |

TABLE 2-continued

Types of K-ras mutations found in the sera of the pancreatic cancer patients.

| Coden | mutation[a] | amino acid change | Number | Mutant melting peak |
|---|---|---|---|---|
| (12) | GGT → G$\underline{TT}$, G$\underline{A}$T[b] (Gly → Val, Asp) | | 1 | Yes |
| Wild-type | | | 5 | No |
| Total | | | 24 | |

[a]Altered bases are underlined.
[b]Two mutations co-exist in the patient.

Discussion

The essence of this invention is the development of a PCR procedure for the detection of gene mutations in trace amounts using PNA as a PCR clamp as well as a sensor probe. The uniqueness of this newly developed method is that PCR amplification, mutant enrichment and mutation detection can be accomplished in a single tube on the LightCycler without the need for several laborious procedures including electrophoresis, hybridization and enzymatic reaction. Next, the $T_m$ difference between perfectly matched templates and mismatched templates is larger for PNA probes than oligonucleotide probes. Therefore, all mutant alleles with single base changes can be readily distinguished from wild-type alleles by melting peak analysis. Most importantly, only one pair of primers and probes are required to detect possible mutations in a selected gene. For example, all 12 possible mutations from the wild-type in codons 12 and 13 of K-ras were successfully detected by the present assay. All these advantages greatly simplify the manipulating procedure and thus can be potentially useful in multiplex assays. Finally, the present assay can detect as low as 10 pg of mutant genomic DNA against a background of 100 ng of wild-type DNA (a 1:10,000 ratio).

PNA is used as both a sensor probe and a PCR clamp in this invention. Association and dissociation of the PNA probe and it complementary DNA are revealed by melting curve analysis. This allows for easy optimization of thermal conditions for PCR clamping of wild-type template but not of mutant templates. The $T_m$ of the PNA probe-wild-type template is 69° C., such that when using conventional PCR at 72° C. for extension, less than half of wild-type templates are associated with the PNA probe, leading us to postulate that the PNA clamp would not be efficient under this temperature.

Based on the results of FIG. 2, the applicants proposed that in order to inhibit the wild-type amplification to a full extent, an extension temperature lower than the wild-type $T_m$, e.g., 60° C., should be used, as it has a minimal effect on mutant amplification. Further, since the $T_m$s of all the mutants studied are between 53 and 60° C., it is supposed that at a temperature above $T_m$, Taq polymerase can readily repel a PNA probe binding and continue the chain elongation.

The fact that primer position also affected the efficiency of clamping is somewhat surprising. One possible explanation is that primer position determines the running-off distance from the PNA binding site. At the extension temperature (60° C.) used in PCR during experiments for K-ras, the progression of Taq polymerase on the wild-type template is hindered because of PNA binding. When reaction temperature ramps from 60° C. (extension) to 94° C. (denaturation phase of the next cycle), the PNA probe leaves the wild-type template at a certain temperature close to its $T_m$ (69° C.) and polymerization resumes. However, the polymerization will occur over a very short time, because the polymerase will quickly dissociate from the template as the temperature continue to rise. If there is too long a distance, the polymerase does not have sufficient time to run off the template. The "chain reaction" of PCR is therefore abolished, because the truncated products, lacking a primer binding site, can no longer serve as templates during the next cycle.

The results also suggest that the ramp rate of a thermal cycler may influence the efficiency of a PNA clamp. The applicants have also found that for a successful clamping, the slower the ramp rate, the longer is the distance required between the priming position of the forward primer and the PNA binding site (C. C. Chiou, unpublished data).

Applying the optimal conditions resulted in the successful detection of mutant K-ras alleles in serum DNA from patients with pancreatic cancer, indicating that the present assay has potential for use in screening malignant diseases in clinical laboratories. Although the method of this invention cannot directly identify specific types of mutation, the amplified PCR products can be subjected to further analysis, such as sequencing, to confirm preliminary findings. Thus, the present assay is useful for research purposes as well.

Note that although mutations occurring in codons 12 and 13 K-ras exon 1 are more likely to be found in cancer patients, other mutations occurring in the flanking region covered by the PNA can also be differentiated by the present assay. The mutation types shown in Table 2 reveal that the majority of K-ras mutations in the tested serum samples are GGT to GTT in codon 12, which is consistent with a previous study indicating that this mutation accounts for 94.5% of pancreatic cancer in the Taiwanese population (J Y. Wang et al. (2002), *Cancer Lett.*, 180:153-158).

PNA in combination with oligonucleotide hybridization probes was used for rapid detection of K-ras mutations in two previous studies, in which a pair of oligonucleotide hybridization probes was used to detect mutations, and a 17-mer PNA was used to suppress PCR of the wild-type allele (J. Däbritz et al. (2005), *Br. J. Cancer*, 92:405-412; C. Y. Chen et al. (2004), *Clin. Chem.*, 50:481-489). Because the PNA bound to DNA so tightly, not only did it suppress PCR, it also competed with the sensor probe for binding to K-ras templates. As a compromise, the investigators designed mutant-specific sensor probes. The perfectly matched mutant, with its high $T_m$ (706° C.), had the largest $T_m$ difference from wild-type (66.3° C.). Other mutants had $T_m$s closer to that of wild-type and were therefore less easily differentiated.

The design of these previous studies and the present invention look similar but utilize very different underlying logic. Specifically, in these previous studies, in addition to the use of "mutant-specific" probes, 72° C. was used as the extension temperature during PCR, leading to inefficient clamping of wild-type amplification. A possible problem with the design of these previous studies is that competition always exists between the PNA and the hybridization probes. The signal is affected by this competition when a mutant is mismatched to both PNA and probe. The extent to which the signal is affected by this competition when a mutant is mismatched to both PNA and probe is not clear.

Recently, another DNA analog, namely locked nucleic acid (LNA), was introduced and used in molecular detection assays (D. A. Braasch and D. R. Corey (2001), *Chem. Biol.*, 8:1-7). PNA and LNA probes have been used in combination to detect genetic heterogeneity of epidermal growth factor receptor (EGFR) in non-small cell lung cancer (Y. Nagai et al. (2005), *Cancer Res.*, 65:7276-7282). In that study, mutant-specific LNA probes were used in a real-time PCR to generate amplification curve, and PNA was used to clamp wild-type amplification. The LNA probes resembled TaqMan probes, with a fluorophore at one end and a quencher at the other end. An amplification curve was generated when the probes were cleaved by Taq DNA polymerase during PCR. Through analysis of the second derivative of the amplification curve, mutants containing a point mutation or a deletion in the EGFR gene were detected in 100 to 1000-fold excess of wild-type alleles. This study suggests that combining different DNA analogs can be used to develop powerful tools for detecting gene alterations.

The present assay may prove to have additional advantages. For example, mutant detection can be quantitative if samples with standard concentrations are assayed in parallel with clinical specimens, which may be useful in some situations for evaluation of the severity of disease. In addition, the PCR products generated in the present assay can be used for further sequencing analysis, or in other enzymatic reactions, after a simple purification step, without interference by the PNA. Furthermore, multiplexed assays can be performed in a single tube as long as the real-time PCR machine can differentiate fluorescent signals between different probes.

In summary, this invention provides a simple method to detect a trace amount of K-ras mutants in large excess of wild-type DNA. The method of this invention has great potential for use in cancer screening, and could be adapted for detection of trace mutants associated with other diseases. This invention has defined important factors affecting the efficiency of PNA-mediated PCR clamping. These findings will facilitate further development of the role of PNA in molecular diagnosis.

All patents and literature references cited in the present specification as well as the references described therein, are hereby incorporated by reference in their entirety. In case of conflict, the present description, including definitions, will prevail.

While the invention has been described with reference to the above specific embodiments, it is apparent that numerous modifications and variations can be made without departing from the scope and spirit of this invention. It is therefore intended that this invention be limited only as indicated by the appended claims.

We claim:

1. A method for determining whether a target polynucleotide sequence contained in a nucleic acid sample has nucleotide variation(s) in a selected region thereof, comprising
providing a pair of a first primer and a second primer which allows the formation of a PCR product comprising a sequence covering that of the selected region of the target polynucleotide sequence via a PCR process,
wherein the first primer comprises a sequence based on that of a first region located upstream of the selected region of the target polynucleotide sequence, wherein the second primer comprises a sequence based on that of a second region located downstream of the selected region of the target polynucleotide sequence,
wherein the 5'-end of the first region is spaced apart from the 5' end of the sequence of the selected region by 30 nucleotides or more;
providing a labeled peptide nucleic acid probe comprising a detectable moiety and comprising a sequence that fully complements to the sequence of the selected region of a reference target polynucleotide sequence comprising no nucleotide variation(s) therein, such that hybridization of the labeled peptide nucleic acid probe to the selected region of said reference target polynucleotide sequence results in the formation of a first duplex having a first melting temperature;
determining the melting temperature of the first duplex;
admixing the labeled peptide nucleic acid probe and said pair of the first and second primers with a nucleic acid sample to form a mixture;
subjecting said mixture to a PCR process including an extension reaction set to run at a temperature lower than the melting temperature of the first duplex by 5 to 20° C., such that PCR products are obtained; and
subjecting the PCR products to a melting analysis to determine melting temperatures of the PCR products,
wherein the presence of at least one melting temperature lower than the first melting temperature of the first duplex is indicative of the nucleotide variation(s) in the selected region of the target polynucleotide sequence contained in the nucleic acid sample.

2. The method according to claim 1, wherein the nucleic acid sample is obtained from an organism and said organism is a virus, bacteria, fungus, plant, or animal.

3. The method according to claim 2, wherein the animal is a mammal.

4. The method according to claim 3, wherein the mammal is human.

5. The method according to claim 1, wherein the target polynucleotide sequence comprises a disorder-associated gene, drug-resistance gene, or virulence gene.

6. The method according to claim 5, wherein the disorder-associated gene is cancer-associated gene or a gene associated with a hereditary disease.

7. The method according to claim 6, wherein the cancer-associated gene is K-ras, H-ras, N-ras, p53 (TP53), CDKN2A (p16), PIC3K, PTEN, RB1, epidermal growth factor receptor gene, BRAF, BRCA1, BRCA2, STK11, or VHL.

8. The method according to claim 7, wherein the cancer-associated gene is K-ras.

9. The method according to claim 1, wherein the nucleotide variation(s) include one or more nucleotide deletion, insertion, substitution, or abnormal methylation.

10. The method according to claim 1, wherein the 5'-end of the sequence of the first region is spaced apart from the 5'-end of the sequence of the selected region by 30 to 2000 nucleotides.

11. The method according to claim 1, wherein the 5'-end of the sequence of the first region is spaced apart from the 5'-end of the sequence of the selected region by 50 to 1500 nucleotides.

12. The method according to claim 1, wherein the 5'-end of the sequence of the first region is spaced apart from the 5'-end of the sequence of the selected region by 50 to 1000 nucleotides.

13. The method according to claim 1, wherein the extension reaction is set to run at a temperature lower than the melting temperature of the duplex by 5 to 18° C.

14. The method according to claim 1, wherein the extension reaction is set to run at a temperature lower than the melting temperature of the duplex by 8 to 18° C.

15. The method according to claim 1, wherein the labeled peptide nucleic acid probe ranges from 8 to 30 mer in length.

16. The method according to claim 1, wherein the moiety is a fluorescent moiety, a photoluminescent moiety, a luminescent moiety, or a chemiluminescent moiety.

17. The method according to claim 16, wherein the moiety is a fluorescent moiety.

18. The method according to claim 17, wherein the fluorescent moiety is fluorescein, rhodamine, FAM, TET, HEX, JOE, TAMA, NTB, TAMRA, ROX, VIC, NED, 4,7-dichloro-fluorescein, 4,7-dichloro-rhodamine, Cy5, Cy3, Texas Red, DABCYL, DABSYL, malachite green, cyanine, LC-Red610, LC-Red640, LC-Red670, LC-Red705, or a derivative thereof.

19. The method according to claim 18, wherein the fluorescent moiety is fluorescein.

20. The method according to claim 17, wherein an anchor probe is added in the admixing step.

21. The method according to claim 20, wherein the anchor probe comprises a fluorescent dye.

22. The method according to claim 21, wherein the fluorescent dye is fluorescein, rhodamine, FAM, TET, HEX, JOE, TAMA, NTB, TAMRA, ROX, VIC, NED, 4,7-dichloro-fluorescein, 4,7-dichloro-rhodamine, Cy5, Cy3, Texas Red, DABCYL, DABSYL, malachite green, cyanine, LC-Red610, LC-Red640, LC-Red670, LC-Red705, or a derivative thereof.

23. The method according to claim 22, wherein the fluorescent dye is LC-Red 640.

* * * * *

SEQUENCE LISTING

<160> NUMBER OF SEQ ID NOS: 10

<210> SEQ ID NO 1
<211> LENGTH: 42
<212> TYPE: DNA
<213> ORGANISM: Artificial Sequence
<220> FEATURE:
<223> OTHER INFORMATION: Primer for PCR-mediated site-directed
      mutagenesis of K-ras gene
<220> FEATURE:
<221> NAME/KEY: misc_feature
<222> LOCATION: (34)..(34)
<223> OTHER INFORMATION: h: a, t, c

<400> SEQUENCE: 1
atgactgaat ataaacttgt ggtagttgga gcthgtggcg ta         42

<210> SEQ ID NO 2
<211> LENGTH: 42
<212> TYPE: DNA
<213> ORGANISM: Artificial Sequence
<220> FEATURE:
<223> OTHER INFORMATION: Primer for PCR-mediated site-directed
      mutagenesis of K-ras gene
<220> FEATURE:
<221> NAME/KEY: misc_feature
<222> LOCATION: (35)..(35)
<223> OTHER INFORMATION: h: a, t, c

<400> SEQUENCE: 2
atgactgaat ataaacttgt ggtagttgga gctghtggcg ta         42

<210> SEQ ID NO 3
<211> LENGTH: 42
<212> TYPE: DNA
<213> ORGANISM: Artificial Sequence

```
<220> FEATURE:
<223> OTHER INFORMATION: Primer for PCR-mediated site-directed
      mutagenesis of K-ras gene
<220> FEATURE:
<221> NAME/KEY: misc_feature
<222> LOCATION: (37)..(37)
<223> OTHER INFORMATION: h: a, t, c

<400> SEQUENCE: 3
atgactgaat ataaacttgt ggtagttgga gctggthgcg ta                     42

<210> SEQ ID NO 4
<211> LENGTH: 42
<212> TYPE: DNA
<213> ORGANISM: Artificial Sequence
<220> FEATURE:
<223> OTHER INFORMATION: Primer for PCR-mediated site-directed
      mutagenesis of K-ras gene
<220> FEATURE:
<221> NAME/KEY: misc_feature
<222> LOCATION: (38)..(38)
<223> OTHER INFORMATION: h: a, t, c

<400> SEQUENCE: 4
atgactgaat ataaacttgt ggtagttgga gctggtghcg ta                     42

<210> SEQ ID NO 5
<211> LENGTH: 24
<212> TYPE: DNA
<213> ORGANISM: Artificial Sequence
<220> FEATURE:
<223> OTHER INFORMATION: Forward primer for PCR of K-ras gene

<400> SEQUENCE: 5
atgactgaat ataaacttgt ggta                                         24

<210> SEQ ID NO 6
<211> LENGTH: 20
<212> TYPE: DNA
<213> ORGANISM: Artificial Sequence
<220> FEATURE:
<223> OTHER INFORMATION: Forward primer for PCR of K-ras gene

<400> SEQUENCE: 6
attaacctta tgtgtgacat                                              20

<210> SEQ ID NO 7
<211> LENGTH: 20
<212> TYPE: DNA
<213> ORGANISM: Artificial Sequence
<220> FEATURE:
<223> OTHER INFORMATION: Forward primer for PCR of K-ras gene

<400> SEQUENCE: 7
tactggtgga gtatttgata                                              20

<210> SEQ ID NO 8
<211> LENGTH: 20
<212> TYPE: DNA
<213> ORGANISM: Artificial Sequence
<220> FEATURE:
<223> OTHER INFORMATION: Reverse primer for PCR of K-ras gene

<400> SEQUENCE: 8
caagatttac ctctattgtt                                              20

<210> SEQ ID NO 9
```

```
<211> LENGTH: 17
<212> TYPE: DNA
<213> ORGANISM: Artificial Sequence
<220> FEATURE:
<223> OTHER INFORMATION: Peptide nucleic acid (PNA) sensor probe for
      K-ras gene
<220> FEATURE:
<221> NAME/KEY: misc_feature
<222> LOCATION: (1)..(1)
<223> OTHER INFORMATION: Labeled with fluorescein at the N-terminus

<400> SEQUENCE: 9
cctacgccac cagctcc                                                17

<210> SEQ ID NO 10
<211> LENGTH: 44
<212> TYPE: DNA
<213> ORGANISM: Artificial Sequence
<220> FEATURE:
<223> OTHER INFORMATION: Anchor probe for K-ras gene
<220> FEATURE:
<221> NAME/KEY: misc_feature
<222> LOCATION: (44)..(44)
<223> OTHER INFORMATION: Labeled with flourescent dye LC-Red 640 at the
      3'end

<400> SEQUENCE: 10
gtccacaaaa tgattctgaa ttagctgtat cgtcaaggca ctct                   44
```